US009585652B2

(12) United States Patent
Kortenbach et al.

(10) Patent No.: US 9,585,652 B2
(45) Date of Patent: *Mar. 7, 2017

(54) ENDOSCOPIC SUTURE SYSTEMS

(71) Applicant: Boston Scientific Scimed, Inc., Maple Grove, MN (US)

(72) Inventors: Juergen A. Kortenbach, Miami Springs, FL (US); Ghaleb Sater, Lynnfield, MA (US); Michael Sean McBrayer, Miami, FL (US); Barry N. Gellman, North Easton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 97 days.

This patent is subject to a terminal disclaimer.

(21) Appl. No.: 13/742,716

(22) Filed: Jan. 16, 2013

(65) Prior Publication Data
US 2013/0211428 A1 Aug. 15, 2013

Related U.S. Application Data

(60) Continuation of application No. 11/398,038, filed on Apr. 4, 2006, now Pat. No. 8,382,774, which is a
(Continued)

(51) Int. Cl.
*A61B 17/04* (2006.01)
*A61B 17/06* (2006.01)
(Continued)

(52) U.S. Cl.
CPC ...... *A61B 17/0485* (2013.01); *A61B 17/0469* (2013.01); *A61B 17/0482* (2013.01);
(Continued)

(58) Field of Classification Search
CPC ... A61B 17/0469; A61B 17/04; A61B 17/047; A61B 17/0482; A61B 17/0483;
(Continued)

(56) References Cited

U.S. PATENT DOCUMENTS 1,037,864 A 9/1912 Carlson et al.
1,815,725 A 7/1931 Pilling et al.
(Continued)

FOREIGN PATENT DOCUMENTS

| EP | 0589409 A1 | 3/1994 |
| WO | 9627331 A1 | 9/1996 |
| WO | 9729694 A1 | 8/1997 |

OTHER PUBLICATIONS

Final Office Action Response for U.S. Appl. No. 13/287,722, filed Oct. 1, 2013, 7 pages.
(Continued)

*Primary Examiner* — Elizabeth Houston
*Assistant Examiner* — Lindsey Bachman
(74) *Attorney, Agent, or Firm* — Brake Hughes Bellermann LLP

(57) ABSTRACT

A surgical instrument for applying sutures to tissue includes a needle deployment mechanism and a catch mechanism. In some embodiments, the needle deployment mechanism employs a linear path. Alternatively, it can employ a curved needle. The surgical instrument may include a rotatable head, a bend, and/or a malleable elongated body member formable into various shapes.

17 Claims, 14 Drawing Sheets

Related U.S. Application Data continuation of application No. 10/365,277, filed on Feb. 12, 2003, now Pat. No. 7,048,749, which is a continuation of application No. 09/579,455, filed on May 26, 2000, now Pat. No. 6,551,329, which is a division of application No. 09/273,117, filed on Mar. 19, 1999, now Pat. No. 6,096,051.

(60) Provisional application No. 60/078,916, filed on Mar. 20, 1998.

(51) Int. Cl.
*A61B 17/062* (2006.01)
*A61B 17/29* (2006.01)
*A61B 17/00* (2006.01)

(52) U.S. Cl.
CPC .... *A61B 17/0625* (2013.01); *A61B 17/06066* (2013.01); *A61B 17/0491* (2013.01); *A61B 17/29* (2013.01); *A61B 2017/00805* (2013.01); *A61B 2017/00946* (2013.01); *A61B 2017/047* (2013.01); *A61B 2017/2929* (2013.01); *Y10S 261/11* (2013.01)

(58) Field of Classification Search
CPC ............ A61B 17/0485; A61B 17/3403; A61B 2017/00637; A61B 2017/00663; A61B 2017/0472; A61B 17/0491; A61M 2025/0092; A61M 2025/0095
USPC .......................................... 606/144, 145–148
See application file for complete search history.

(56) References Cited

U.S. PATENT DOCUMENTS

| | | | |
|---|---|---|---|
| 1,822,330 A | 9/1931 | Ainslie | |
| 3,013,559 A | 12/1961 | Thomas | |
| 3,160,157 A | 12/1964 | Chisman | |
| 3,470,875 A | 10/1969 | Johnson | |
| 3,638,653 A | 2/1972 | Berry | |
| 3,946,740 A | 3/1976 | Bassett | |
| 3,986,468 A | 10/1976 | Szostak et al. | |
| 4,579,072 A | 4/1986 | Koike et al. | |
| 4,621,640 A | 11/1986 | Mulhollan et al. | |
| 4,802,798 A | 2/1989 | Adamson | |
| 4,890,615 A | 1/1990 | Caspari et al. | |
| 4,909,798 A * | 3/1990 | Fleischhacker ... | A61M 39/0606 137/846 |
| 5,059,201 A | 10/1991 | Asnis | |
| 5,289,963 A | 3/1994 | McGarry et al. | |
| 5,342,374 A | 8/1994 | Wan et al. | |
| 5,350,385 A | 9/1994 | Christy | |
| 5,364,408 A | 11/1994 | Gordon | |
| 5,381,943 A | 1/1995 | Allen et al. | |
| 5,383,877 A * | 1/1995 | Clarke ............... | A61B 17/0469 606/139 |
| 5,387,221 A | 2/1995 | Bisgaard | |
| 5,389,103 A | 2/1995 | Melzer et al. | |
| 5,413,272 A | 5/1995 | Green et al. | |
| 5,417,699 A | 5/1995 | Klein et al. | |
| 5,437,682 A | 8/1995 | Grice et al. | |
| 5,447,512 A | 9/1995 | Wilson et al. | |
| 5,447,513 A | 9/1995 | Davison et al. | |
| 5,448,989 A | 9/1995 | Heckele | |
| 5,458,609 A | 10/1995 | Gordon et al. | |
| 5,485,952 A | 1/1996 | Fontayne | |
| 5,496,334 A | 3/1996 | Klundt et al. | |
| 5,497,513 A | 3/1996 | Arabeyre et al. | |
| 5,527,321 A | 6/1996 | Hinchcliffe | |
| 5,540,704 A * | 7/1996 | Gordon ............. | A61B 17/0482 112/169 |
| 5,562,686 A | 10/1996 | Sauer et al. | |
| 5,569,269 A * | 10/1996 | Hart et al. ..................... | 606/144 |
| 5,573,542 A | 11/1996 | Stevens | |
| 5,578,044 A | 11/1996 | Gordon et al. | |
| 5,582,615 A | 12/1996 | Foshee et al. | |
| 5,586,986 A | 12/1996 | Hinchcliffe | |
| 5,643,294 A | 7/1997 | Tovey et al. | |
| 5,662,664 A | 9/1997 | Gordon et al. | |
| 5,662,666 A | 9/1997 | Onuki et al. | |
| 5,665,096 A | 9/1997 | Yoon | |
| 5,673,841 A | 10/1997 | Schulze et al. | |
| 5,713,910 A | 2/1998 | Gordon et al. | |
| 5,730,747 A | 3/1998 | Ek et al. | |
| 5,746,753 A | 5/1998 | Sullivan et al. | |
| 5,749,828 A | 5/1998 | Solomon et al. | |
| 5,755,727 A | 5/1998 | Kontos | |
| 5,807,241 A | 9/1998 | Heimberger | |
| 5,843,001 A | 12/1998 | Goldenberg | |
| 5,855,585 A | 1/1999 | Kontos | |
| 5,860,991 A | 1/1999 | Klein et al. | |
| 5,871,204 A | 2/1999 | Spirer | |
| 5,897,572 A | 4/1999 | Schulsinger et al. | |
| 5,910,148 A | 6/1999 | Reimels et al. | |
| 5,911,727 A | 6/1999 | Taylor | |
| 5,916,146 A | 6/1999 | Allotta et al. | |
| 5,927,162 A | 7/1999 | Huang | |
| 5,951,575 A | 9/1999 | Bolduc | |
| 5,957,937 A | 9/1999 | Yoon | |
| 5,972,000 A | 10/1999 | Beyar et al. | |
| 5,972,013 A * | 10/1999 | Schmidt ......................... | 606/185 |
| 5,984,932 A * | 11/1999 | Yoon .............................. | 606/147 |
| 5,993,466 A | 11/1999 | Yoon | |
| 6,051,006 A | 4/2000 | Shluzas et al. | |
| 6,059,800 A * | 5/2000 | Hart ................... | A61B 17/0469 606/139 |
| 6,096,051 A | 8/2000 | Kortenbach et al. | |
| 6,364,828 B1 | 4/2002 | Yeung et al. | |
| 6,454,778 B2 | 9/2002 | Kortenbach | |
| 6,551,329 B1 | 4/2003 | Kortenbach et al. | |
| 6,592,610 B2 | 7/2003 | Beyar | |
| 8,758,232 B2 | 6/2014 | Graham et al. | |
| 2005/0075538 A1 | 4/2005 | Banik et al. | |
| 2005/0131279 A1 | 6/2005 | Boulais et al. | |
| 2005/0272978 A1 | 12/2005 | Brunnen et al. | |

OTHER PUBLICATIONS

Final Office Action for U.S. Appl. No. 13/287,722, mailed Jul. 1, 2013, 14 pages.
Final Office Action for U.S. Appl. No. 13/287,722, mailed on Oct. 23, 2014, 9 pages.
Response to Final Office Action for U.S. Appl. No. 13/287,722, filed Jan. 23, 2015, 10 pages.
Final Office Action for U.S. Appl. No. 13/401,148, mailed on Feb. 4, 2015, 10 pages.
Non-Final Office Action for U.S. Appl. No. 13/287,722, mailed Mar. 25, 2014, 9 pages.
Restriction Requirement for U.S. Appl. No. 13/401,148, mailed on Jun. 2, 2014, 6 pages.
Response to Restriction Requirement for U.S. Appl. No. 13/401,148, filed Aug. 1, 2014, 2 pages.
Non-Final Office Action for U.S. Appl. No. 13/401,148, mailed on Sep. 19, 2014, 10 pages.
Non-Final Office Action for U.S. Appl. No. 13/401,148, mailed on Oct. 19, 2015, 12 pages.
Final Office Action for U.S. Appl. No. 13/401,148, mailed Mar. 17, 2016, 15 Pages.
Response to Final Office Action for U.S. Appl. No. 13/401,148, filed May 17, 2016, 8 pages.

* cited by examiner

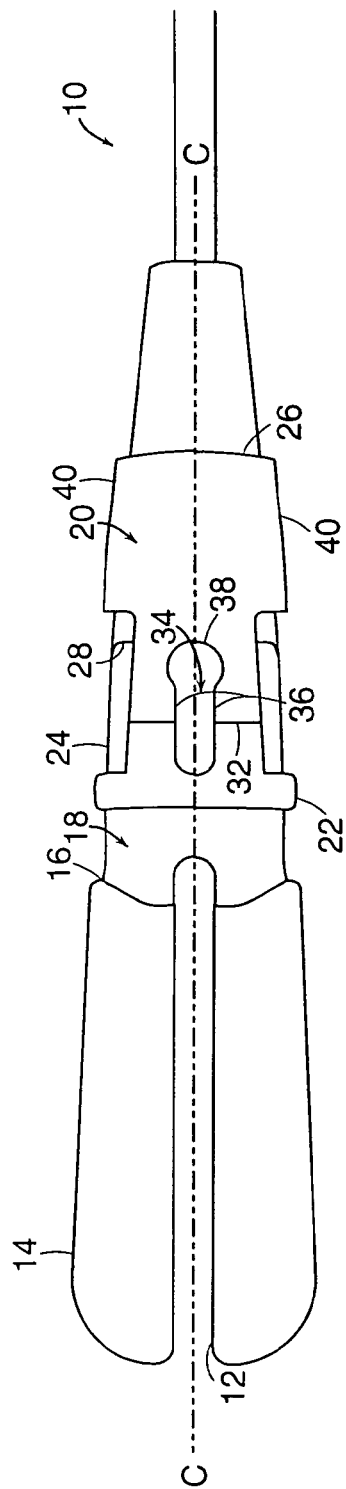
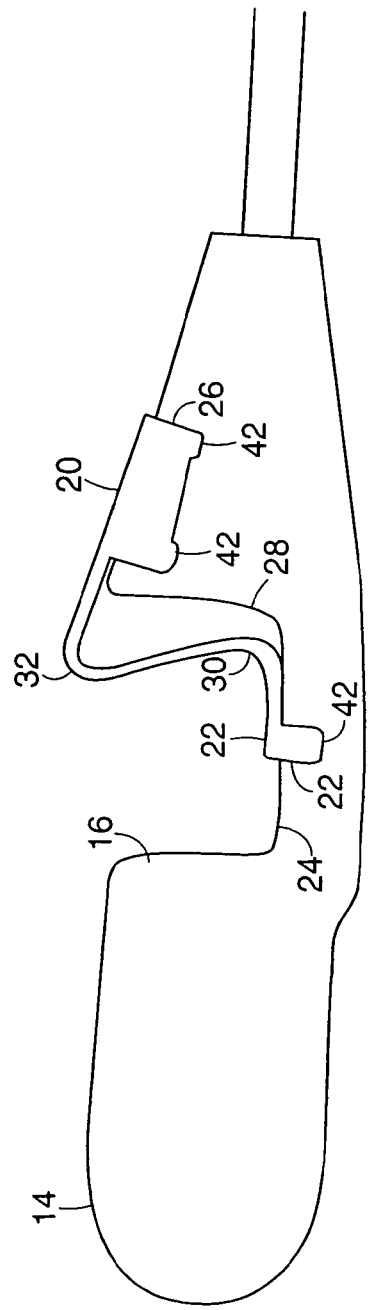
FIG. 1A
FIG. 1B

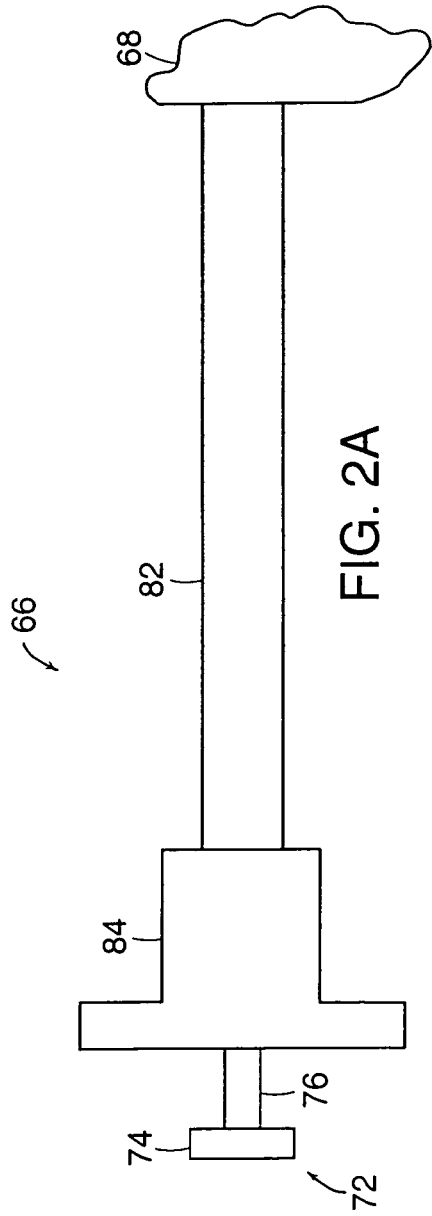
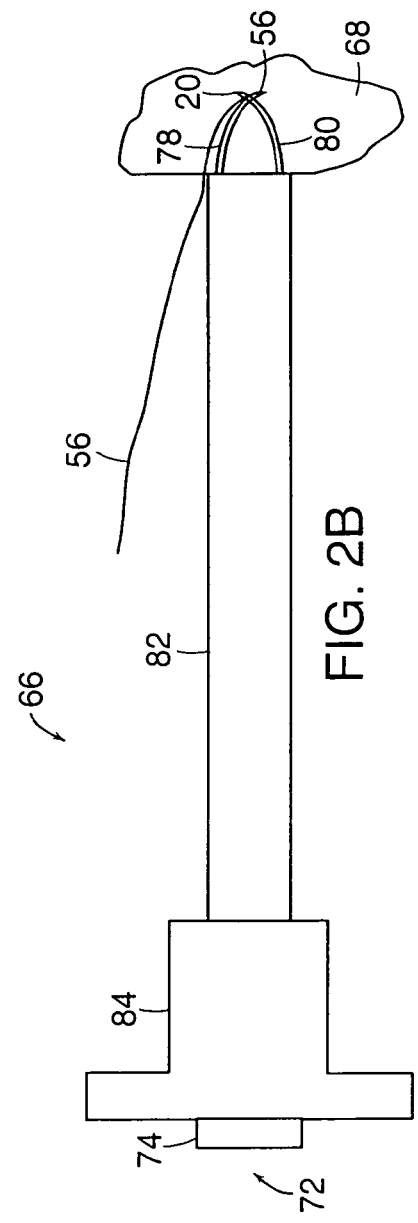

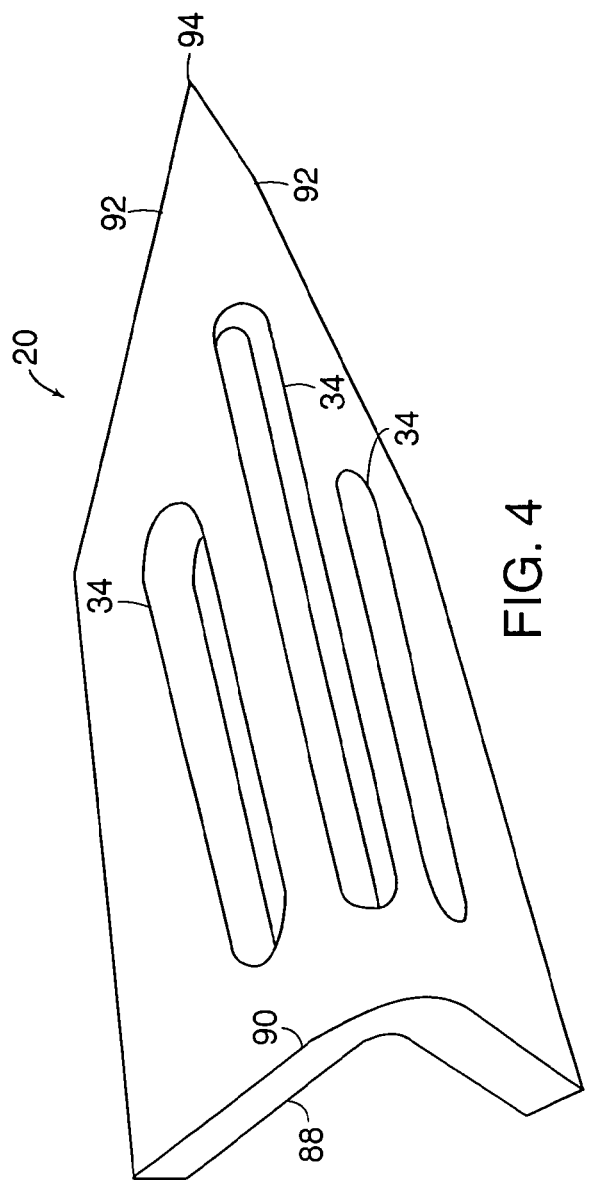

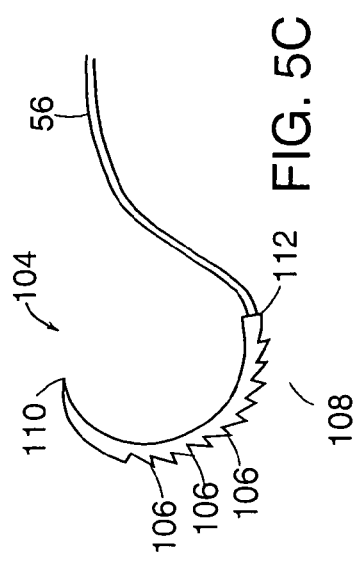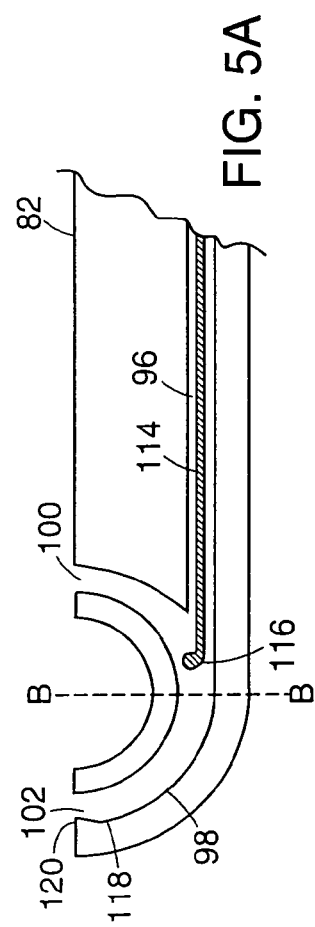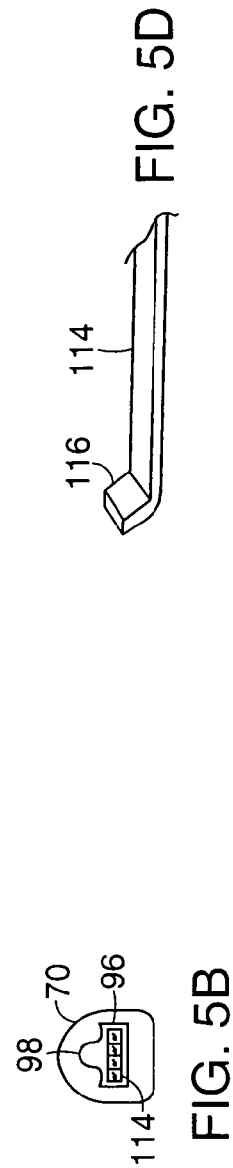

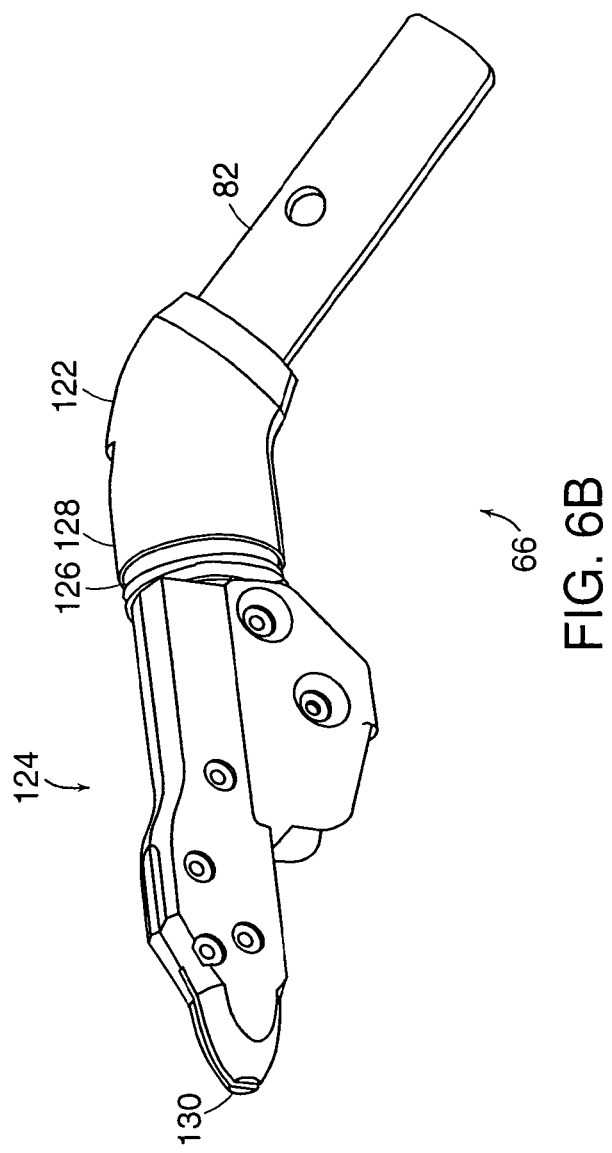

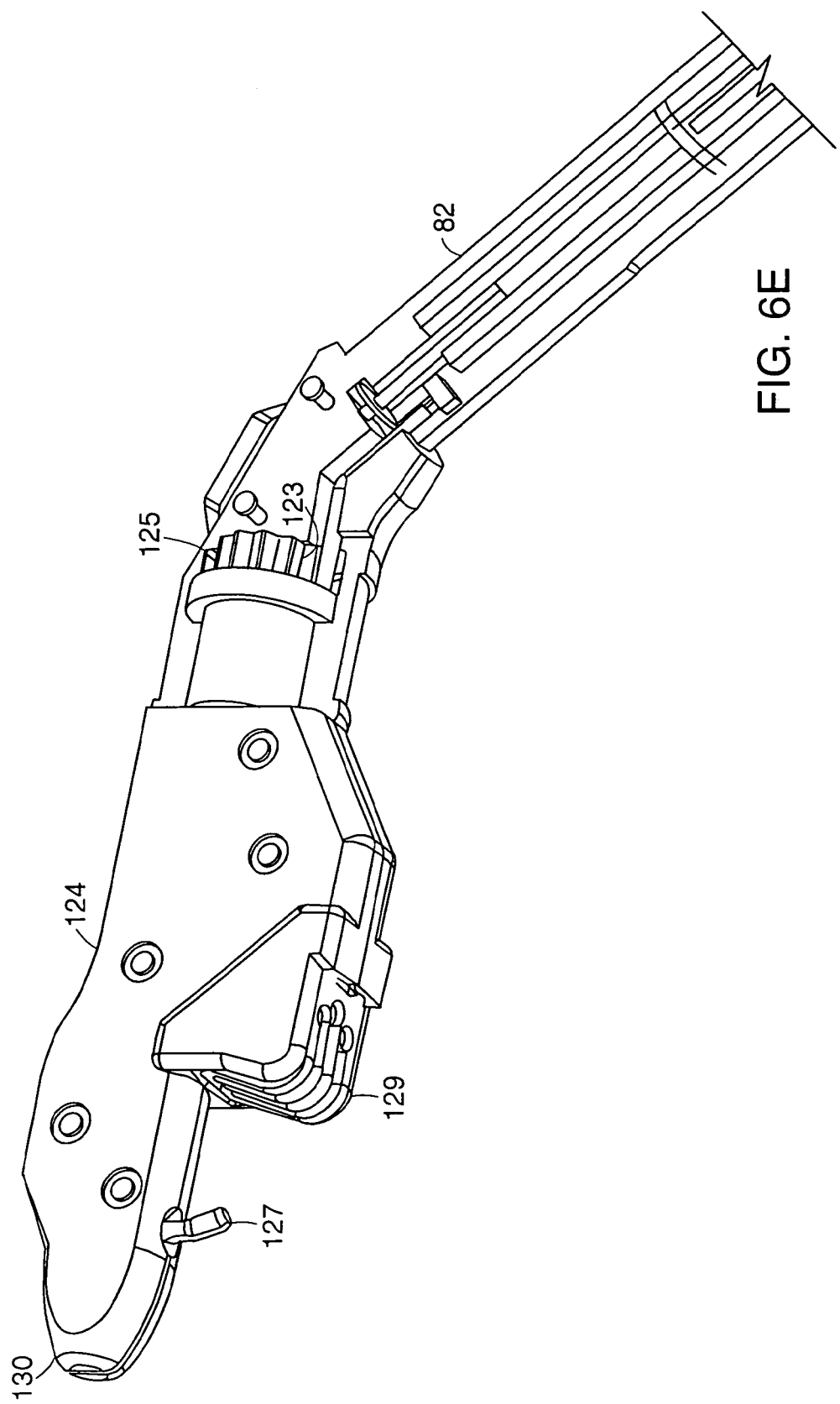

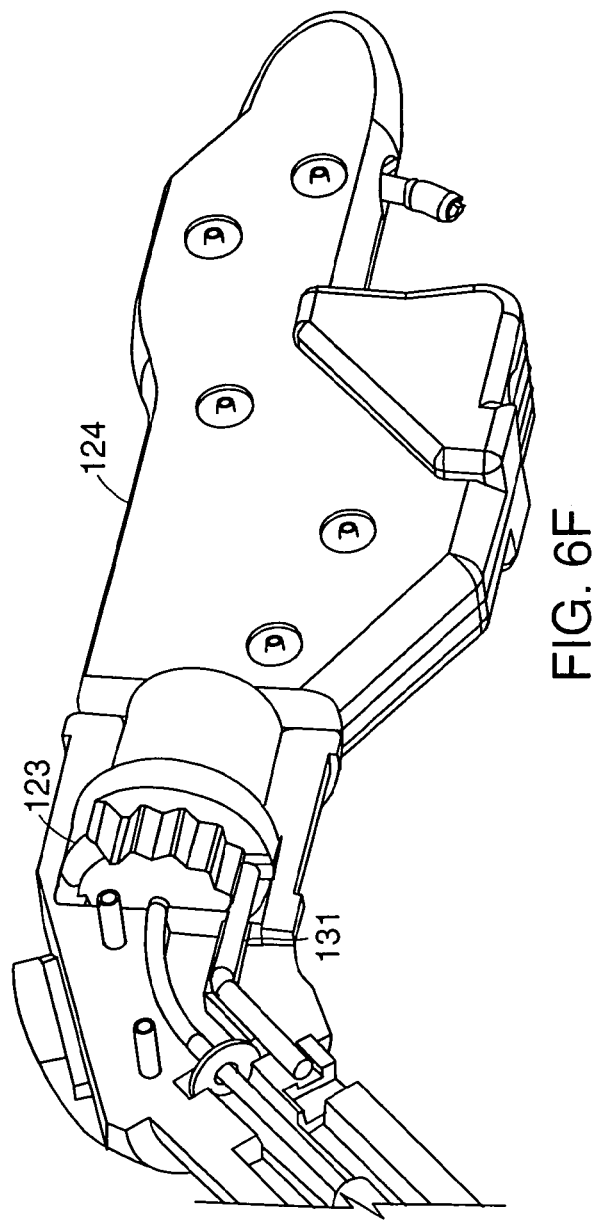

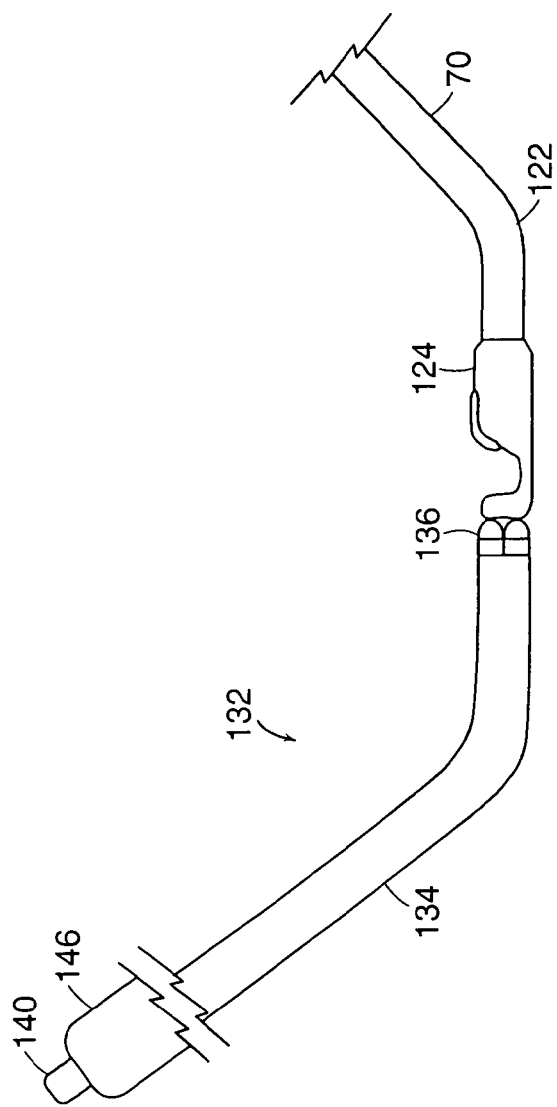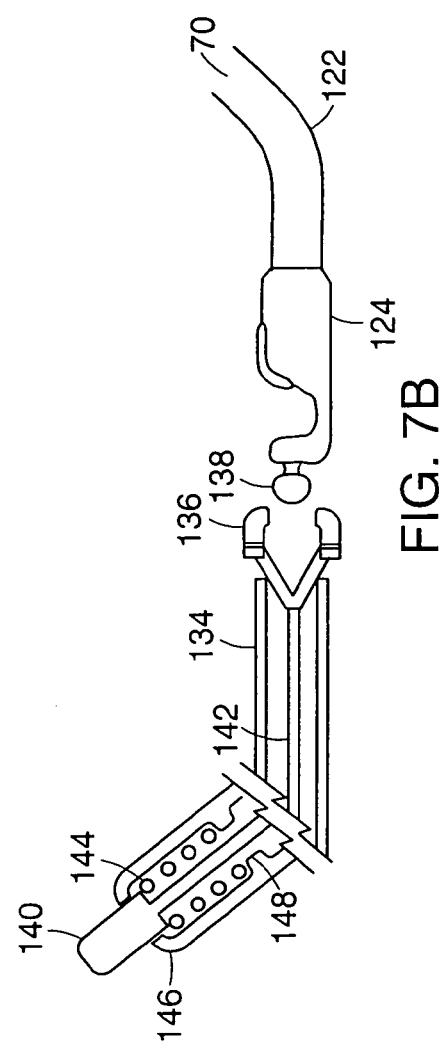

ENDOSCOPIC SUTURE SYSTEMS

CROSS-REFERENCE TO RELATED APPLICATIONS

This is a continuation of U.S. Ser. No. 11/398,038, filed on Apr. 4, 2006, now U.S. Pat. No. 8,382,774, which is a continuation of U.S. Ser. No. 10/365,277, filed Feb. 12, 2003, now U.S. Pat. No. 7,048,749, which is a continuation of U.S. Ser. No. 09/579,455, filed May 26, 2000, now U.S. Pat. No. 6,551,329, which is a divisional of U.S. Ser. No. 09/273,117, filed Mar. 19, 1999, now U.S. Pat. No. 6,096,051, which claims the benefit of and priority to provisional U.S. Ser. No. 60/078,916, filed Mar. 20, 1998. In addition, related U.S. Ser. No. 09/925,957, filed Aug. 9, 2001, now U.S. Pat. No. 6,454,778, is a continuation of U.S. Ser. No. 09/579,455, filed May 26, 2000, now U.S. Pat. No. 6,551,329, which is a divisional of U.S. Ser. No. 09/273,117, filed Mar. 19, 1999, now U.S. Pat. No. 6,096,051, which claims the benefit of and priority to provisional U.S. Ser. No. 60/078,916, filed Mar. 20, 1998. The entire contents of all of the above-referenced applications and patents are incorporated herein by reference.

TECHNICAL FIELD

The invention generally relates to surgical instruments for applying sutures to tissue. More particularly, the invention relates to needle deployment mechanisms and catch mechanisms.

BACKGROUND INFORMATION

Suturing of body tissue is a time consuming aspect of many surgical procedures. For many surgical procedures, it is necessary to make a large opening in the human body to expose the area that requires surgical repair. There are instruments available that allow for viewing of certain areas of the human body through a small puncture wound without exposing the entire body cavity. These instruments, called endoscopes, can be used in conjunction with specialized surgical instruments to detect, diagnose and repair areas of the body that previously required open surgery to access.

Currently, most surgical instruments used in endoscopic procedures are limited by the manner in which they access the areas of the human body in need of repair. In particular, the instruments may not be able to access tissue or organs located deep within the body or that are in some way obstructed. Also, many of the instruments are limited by the way they grasp tissue, apply a suture, or recapture the needle and suture. In addition, many of the instruments are complicated and expensive to use due to the numerous parts and/or subassemblies required to make them function properly.

SUMMARY OF THE INVENTION

The present invention generally is directed to medical instruments for inserting a suture through body tissue in a quick and easy manner using needle deployment mechanisms and catch mechanisms. In some embodiments, the needle deployment mechanism employs a linear needle path. In other embodiments, the needle deployment mechanism employs a curved needle path. Some embodiments of the needle deployment and catch mechanism include a rotatable head.

The instruments of the present invention are useful for application of sutures to approximate the sides of a tissue wound in; for example, open, mini-incision, trans-vaginal, or endoscopic surgical procedures. These instruments may be used in surgical procedures such as burch colposuspension, sacrospinous vaginal vault suspension, paravaginal repair, radical prostatectomy, sub-urethral sling, oopherectomy, myomectomy, nissen fundoplication, cholecystectomy, and urethral anastomosis, for example.

In one aspect, the invention relates to a suturing instrument comprising an elongated body member, a head, and a needle carrier. The head extends from a distal end of the elongated body member, and the head defines a longitudinal groove and an opening in communication with the longitudinal groove. The head also includes a needle catch disposed within the opening. The needle carrier is for holding a needle, and the needle carrier is disposed and movable within the longitudinal groove to advance linearly the needle into the opening and towards the needle catch.

Embodiments according to this aspect of the invention can include the following features. The needle carrier can define a needle holder and a recess for suture material. The needle carrier can include a U-bend. The needle catch can include an opening with at least two flexible edges. The suturing instrument can include a handle located opposite the distal end of the elongated body member, and the handle can include an actuator coupled to the needle carrier.

In another aspect, the invention relates to a suturing instrument comprising an elongated body member, a needle catch, and a needle carrier. The needle catch includes at least one opening for receiving a needle, and the needle catch is movable from within the elongated body member to outside of the elongated body member. The needle carrier is for holding the needle, and the needle carrier is movable from within the elongated body member to outside of the elongated body member.

Embodiments according to this aspect of the invention can include the following features. The suturing instrument can include a pusher movably disposed within the elongated body member and coupled to the needle carrier and needle catch. The suturing instrument can also include a needle catch driver coupled to the pusher and the needle catch and/or a needle carrier driver coupled to the pusher and the needle carrier. The pusher can move the needle carrier and needle catch from within the elongated body member to outside the elongated body member. The pusher can move the needle carrier and needle catch towards each other, and in one embodiment, the needle carrier and needle catch can intersect. In addition, the suturing instrument can include a distal end with an inner taper to direct the needle carrier and needle catch towards each other when moved from within the elongated body member to outside the elongated body member. The needle carrier can include a needle holder and a recess for suture material located it its distal end. The needle catch can include a point for tissue penetration.

In yet another aspect, the invention relates to a suturing instrument comprising an elongated body member, a curved needle, and a pusher. The elongated body member includes a distal portion and defines a curved channel within the distal portion. The curved needle includes a series of notches and is receivable within the curved channel. The pusher is movably disposed within the elongated body member and contacts the notches of the needle to advance the needle out of the curved channel.

Embodiments according to this aspect of the invention can include the following features. The curved channel and/or the curved needle can comprise a semi-circular shape.

The series of notches disposed on the curved needle can be located on the needle's concave or convex surface. The suturing instrument can define an opening leading to the curved channel and a protruding edge at the opening for engaging the series of notches of the needle.

In still another aspect, the invention relates to a suturing instrument comprising an elongated body member and a head. The elongated body member includes a first engaging element located at its distal end. The head includes a second engaging element located at its proximal end that engages with the first engaging element of the elongated body member to position the head in one of a plurality of orientations with respect to the elongated body member.

Embodiments according to this aspect of the invention can include the following features. The first engaging element can include a female configuration, and the second engaging element can include a male configuration for mating with the first engaging element. Alternatively, the first engaging element can include a male configuration and the second engaging element can include a female configuration for mating with the first engaging element. The female configuration can include a series of notches and/or a flexible detent for engaging the male configuration, and the male configuration can include a series of protuberances, notches, and/or fluted cuts for engaging the female configuration. The head of the suturing instrument can be secured in position by engaging the first and second engaging elements, and the head can be rotated when the first and second engaging elements are disengaged. Alternatively, the head can be positioned by rotating one engaging element with respect to the mating engaging element, and in this configuration the head is secured in place by mechanical engagement of the two engaging elements. The head can be rotated with respect to the body member in increments as small as 10°. The head can include a needle deployment mechanism and a catch mechanism located at its distal end, and the distal end can be bullet-shaped to maintain a body lumen in a dilated state.

Additional embodiments according to any of the foregoing aspects of the invention can include the following features. The elongated body member of the suturing instrument can be adapted to access remote tissue or organs within the body. The elongated body member can include a bend or bends. The bend can take the shape of an elbow, a soft curve, a double curve, or any other shape suited to access remote organs or tissue within the body. The elongated body member can be preshaped and permanently bent and comprised of sturdy or resilient material. The elongated body member can also be comprised of a malleable material and thus be bent and shaped to a desired form. The shaping can be done manually outside the body, or remotely within the body to fit the required course for the instrument.

In still yet another aspect, the invention relates to a needle catch for use with a suturing instrument. The needle catch includes at least one opening for receiving a needle, and the needle catch includes a point for tissue penetration. The point can be formed by at least two tapered edges. The needle catch can also be bent to include convex and concave surfaces, and the needle catch can comprise stainless steel.

These and other objects, along with advantages and features of the present invention herein disclosed, will become apparent through reference to the following description of embodiments of the invention, the accompanying drawings, and the claims.

BRIEF DESCRIPTION OF THE DRAWINGS

In the drawings, like reference characters generally refer to the same parts throughout the different figures. Also, the drawings are not to scale; emphasis instead generally being placed upon illustrating the principles of the invention.

FIG. 1A is a top view of the distal end of one embodiment of the suturing system according to the invention.

FIG. 1B is a side view of the distal end of one embodiment of the suturing system according to the invention featuring a Z-bend needle catch.

FIG. 2A is a schematic representation of one embodiment of the invention for suturing transversely positioned tissue.

FIG. 2B is another schematic representation of one embodiment of the invention for suturing transversely positioned tissue.

FIG. 4 is a perspective view of one embodiment of a needle catch for use with the suturing system of FIGS. 2 and 3.

FIG. 5A is a longitudinal section view of the distal end of one embodiment of the suturing system of the invention.

FIG. 5B is a cross-section view of the distal end of one embodiment of the suturing system of the invention taken at line B-B.

FIG. 5C is a side view of one embodiment of a needle with suture.

FIG. 5D is a perspective side view of one embodiment of a pusher.

FIGS. 6A-6C are schematic, perspective, side-view representations of one embodiment of the suturing system of the invention featuring an elbow-shaped, elongated body member with a rotatable head shown in various rotated positions, but not showing a needle deployment mechanism or a needle catch mechanism.

FIGS. 6D-6F are schematic representations of some details of the rotatable head shown in FIGS. 6A-6C and featuring a needle deployment mechanism, a needle catch mechanism, and the engaging elements.

FIG. 7A is a schematic representation of one embodiment of a suturing system of the present invention featuring an elbow-shaped, elongated body member with a rotatable suturing head used in connection with a grasper.

FIG. 7B is a schematic representation of one embodiment of a suturing system of the present invention showing a sectional view of the grasper in the extended position.

DESCRIPTION

Figure 1D:
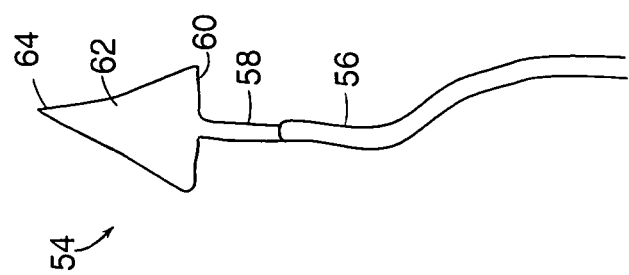
FIG. 1D is a side view of an embodiment of a needle and suture for use with the invention.

In general, the present invention is directed to various improvements of components and mechanisms of needle deployment systems for suturing devices, such as those disclosed in U.S. Pat. No. 5,713,910 to Gordon et al., U.S. Pat. No. 5,578,044 to Gordon et al., U.S. Pat. No. 5,575,800 to Gordon, U.S. Pat. No. 5,540,704 to Gordon et al., U.S. Pat. No. 5,458,609 to Gordon et al., and U.S. Pat. No. 5,364,408 to Gordon, all of which are incorporated herein by reference in their entirety.

Referring to FIGS. 1A and 1B, the distal end 10 of one embodiment of a suturing system according to the present invention defines a distal longitudinal groove 12 located at the tip 14 of the distal end 10 and intersecting with the distal wall 16 of an opening 18. The suturing system can include a handle located opposite the distal end of the elongated body member. The handle could take a variety of forms, for example, the handle could be one of the types used with Boston Scientific Corporation suturing systems, in particular the Laurus-Capio Push & Catch suturing system. The distal end 10 may be fabricated from molded or machined plastic material such as polycarbonate or glass-filled polycarbonate. Located within the opening 18 and in a plane substantially perpendicular to the needle carrier 44 path is a needle catch 20 having a distal side 22 resting on the floor 24 of the opening 18 and a proximal side 26 resting against the proximal wall 28 of the opening 18. Between the two sides 22 and 26, the needle catch 20 forms a concave bend 30 proximal to side 22 and a convex bend 32 proximal to side 26 forming a Z-like shape. Between the two sides 22 and 26 of the needle catch 20 and aligned with the distal longitudinal groove 12 is an opening 34 formed by two flexible edges 36 and a mouth 38. The lateral sides 40 of the needle catch 20 wrap around the distal end 10 of the suturing system and are secured in place by notches 42 turned inward into the body of the distal end, or alternatively into small grooves. The needle catch 20 is preferably made of thin stainless steel material, in particular, high temper stainless steel. The needle catch may be manufactured by stamping, laser machining or chemical etching, for example.

Figure 1C:
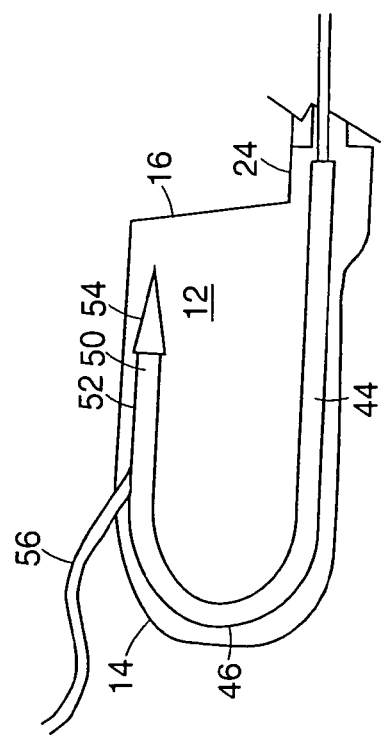
FIG. 1C is a longitudinal section view of the distal end of one embodiment of the suturing system according to the invention taken along line C-C.

Referring to FIG. 1C, in the longitudinal groove 12 is positioned a needle carrier 44 having a convex U-bend 46. At the end 48 of the needle carrier is a needle holder 50 that defines a hole with a recess 52 for lodging the needle 54 and suture 56. When the needle carrier 44 is actuated along the longitudinal axis of the elongated body member, the needle carrier 44 advances the needle 54 linearly from the distal end of the longitudinal groove 12, through the tissue located within the opening 18, and into the needle catch 20. The release of the needle 54 from the needle carrier 44 occurs upon reverse motion of the needle carrier 44.

Referring to FIG. 1D, suitable needles 54 for positioning into the needle holder 50, include a neck 58 with a hole at one of its ends for inserting a suture 56 and at least one shoulder 60. The body 62 of the needle 54 is tapered from the shoulder 60 to the point 64 to facilitate tissue penetration and insertion into the opening 34 of the needle catch 20. The shoulders 60 are made of larger dimensions than the opening 34 of the needle catch 20. During insertion of the needle 54 into the opening 34 of the needle catch 20, the edges 36 of the opening 34 flex upon pressure exerted by the body 62 of the needle 54 at the shoulders 60 and permit entry of the needle 54 into the opening 34. The needle 54 is retained within the needle catch 20 when the edges 36 return to their original position once the shoulders 60 have entered the opening 34 and the neck 58 of the needle 54 is lodged in the opening 34. Preferably, the neck 58 has smaller dimensions than the opening 34 to permit the edges 36 to return to their original position. The needle 54 is released from the needle catch 20 by sliding the neck 58 of the needle 54 toward the mouth 38 of the opening 34. The dimensions of the mouth 38 are larger than the dimensions of the shoulders 60 to permit the release of the needle 54 from the needle catch 20.

Needle deployment/catch systems as described in FIGS. 1A-1C can be made with various dimensions as necessary for a specific application. In particular, this instrument is well suited to being made to minute dimensions. For example, suitable dimensions to use for a instrument for performing an urethral anastomosis can be as follows: the tip 14 may be 1.15 in. long, 0.205 inch wide, and 0.275 in. high; the distal end 10 may be 0.058 in. in diameter; the needle carrier 44 may be 0.032 in. in diameter; the distance between the distal wall 16 of the opening 18 to the opening 30 of the needle catch 20 may be 0.15 in. long.

One advantage of the suturing system/instrument of FIGS. 1A-1D is that it requires fewer parts; thereby, making it easier and less expensive to manufacture than known devices.

Referring to FIGS. 2A and 2B, in another embodiment of the suturing instrument 66 according to the present invention, the instrument is configured to deploy a needle 54 through tissue 68 positioned substantially perpendicular to the elongated body member 82 of the suturing instrument 66. The suturing instrument comprises a pusher 72 having a knob 74 at the proximal end and an elongated portion 76 extending from the knob 74 to the distal end and connected to the needle carrier driver 78 and the needle catch driver 80. The elongated portion 76 of the pusher 72 is positioned within an elongated body member 82, which includes a tubular body 70 that extends from the proximal end to the distal end where it contacts the tissue 68 to be sutured. The elongated body member 82 includes a handle portion 84 located at the proximal end that provides grip for manipulation of the instrument and support for actuating the pusher 72.

In the retracted position, as shown in FIG. 2A, the tissue 68 to be sutured is positioned at the distal end of, and substantially perpendicular to, the elongated body member 82. The needle carrier 44 and the needle catch 20 are positioned within the elongated body member 82, and the knob 76 is afar from the handle portion 84 of the elongated body member 82. In an extended position, as shown in FIG. 2B, the needle carrier 44 holding a needle 54 and the needle catch 20 are moved to a position outside the elongated body member 82 and into the tissue 68. The needle carrier 44 and the needle catch 22 can be moved simultaneously by the needle carrier driver 78 and the needle catch driver 80 when actuated by the pusher 72. The needle carrier 44 and the needle catch 22 meet afar from the distal end of the elongated body member and into the tissue 68 such that the needle 54 with a suture 56 attached thereto is pushed through the opening 34 of the needle catch 20 until the shoulders 60 of the needle 54 snap there through. In the extended position, the knob 74 of the pusher 72 is proximal to, and in contact with, the handle 84 of the elongated body member 82. The suture 56 and the needle 54 are brought back out of the tissue 68 with the needle catch 20 when the suturing system is returned to its retracted position. To facilitate return to the retracted position, the knob 74 of the pusher 72 may alternatively comprise a ring for insertion of a finger by the operator of the instrument.

Figure 3A:
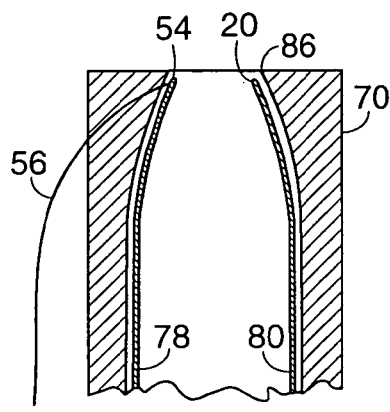
FIG. 3A is a section view of the distal end of the suturing system of the embodiment shown in FIGS. 2A and 2B in the retracted position.
Figure 3B:
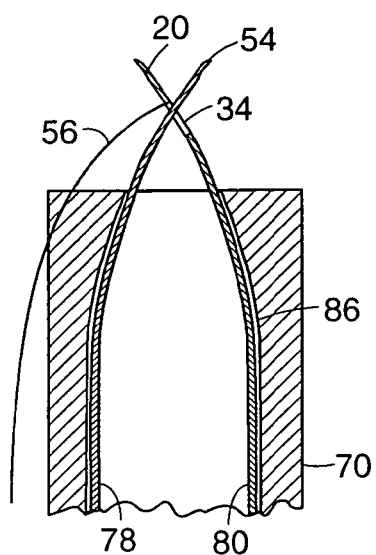
FIG. 3B is a section view of the distal end of the suturing system of the embodiment shown in FIGS. 2A and 2B in the extended position.

Referring to FIGS. 3A and 3B, showing a longitudinal section of the distal end of a particular embodiment of a suturing instrument 66, the interior wall 86 of the elongated body member 82 tapers inward at the distal end. When the pusher 72 is depressed, moving from afar towards the handle 84, the elongated portion of the pusher 72 pushes simultaneously the needle carrier driver 78 and the needle catch driver 80 towards their extended position. The tapered interior wall 86 directs both, the needle carrier 44 and the needle catch 20 towards each other when pusher 72 is depressed.

Alternatively, the needle carrier driver 78 and needle catch 80 can be prebent or include a pivotal system such as a pivot pin or scissors so that the paths of the needle carrier 44 and the catch 20 run from separated lateral positions within the elongated body member 82 to an intersecting point outside the elongated body member 82. In the fully extended position, shown in FIG. 3B., the needle 54 has been pushed through the opening 34 of the needle catch 20 within the tissue 68 to be sutured. When the suturing instrument 66 is returned to its retracted position, as shown in FIG. 3A, the needle 54 is retained by the needle catch 20 and drawn out of the tissue 68. The needle 54 can then be released from the needle catch 20 by pulling the needle 54 and cutting the suture 56 off.

A needle catch 20, suitable for use in the suturing instrument 66 shown in FIGS. 2A and 2B, is shown in FIG. 4. The needle catch 20 is preferably made of a sheet of stainless steel which is bent to provide a concave surface 88 and a convex surface 90 for rigidity. The needle catch 20 can contain several openings 34. The needle catch 20 also comprises two tapered sides 92 that merge into a point 94 for easy penetration of tissue 68. The needle catch 20 can be mounted and secured to the needle catch driver 80 either by permanent bond using glue or any known interlocking system such as pressure snap-in.

Referring to FIGS. 5A-5D, in another embodiment of the invention the suturing instrument includes an elongated body member 82 having a channel 96 extending from the head portion to the distal end. FIG. 5A shows a longitudinal sectional view of the distal end of the suturing instrument 66 with the distal end of channel 96 intersecting tangentially with a curved guiding channel 98. The guiding channel 98 is positioned along the longitudinal axis of the elongated body member 82 and defines two openings 100, 102 on the lateral side of the elongated body member 82. The proximate opening 100 permits ingress of a needle 104 (shown in FIG. 5C) having a curved shape and a series of notches 106 on a portion of the convex surface 108. The point 110 of the needle having smooth surfaces and being tapered to facilitate penetration of tissue 68. The tail 112 of the needle 104 having a hole to permit fixation of the suture material 56.

Referring to FIGS. 5A and 5B, a pusher 114 is positioned in the longitudinal channel 96 with the head 116 forming an edge to provide support and engage into the notches 106 of the needle 104 introduced into the guiding channel 98.

On the outer wall 118 of the distal opening 102 is positioned a protruding edge 120 that provides for locking of the needle 104 during egress from the guiding channel 98. Each push of the pusher 114 moves the needle 104 within the guiding channel 98 from the proximal opening 100 to the distal opening 102 until a notch 106 locks onto the protruding edge 120. A pull of the pusher 114 slides the head 116 of the pusher 114 against the sliding sides of the notches 106 until it engages in a notch 106 closer to the tail 112 of the needle. The push and pull motion is repeated several times until all of the needle 104 has passed through the guiding channel 98, and into tissue positioned parallel to, and in contact with, the distal opening 102. The needle 104 can then be extracted from the tissue once the point 110 resurfaces out of the mass of the tissue with surgical pliers, tweezers, hemostats, needle holders, or other appropriate surgical instrument.

FIG. 5B shows a cross-sectional view of the distal end of the suturing instrument at the intersection between the longitudinal channel 96 and the guiding channel 98.

FIG. 5D shows a prospective view of the pusher 114 with the head 116.

Figure 6A:
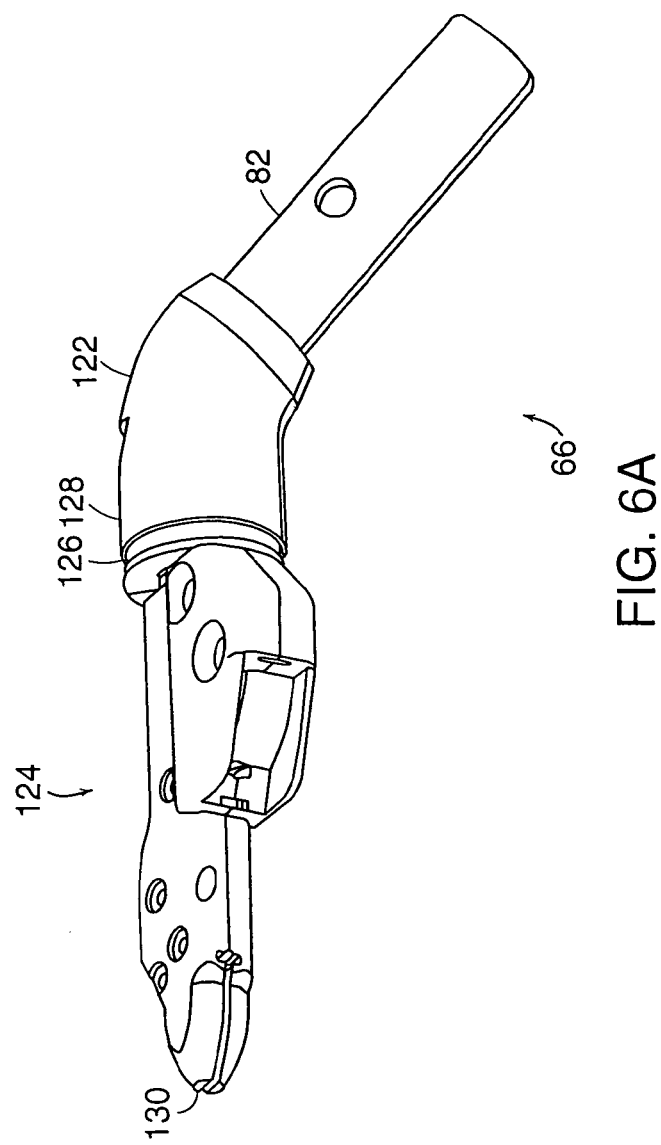
Figure 6C:
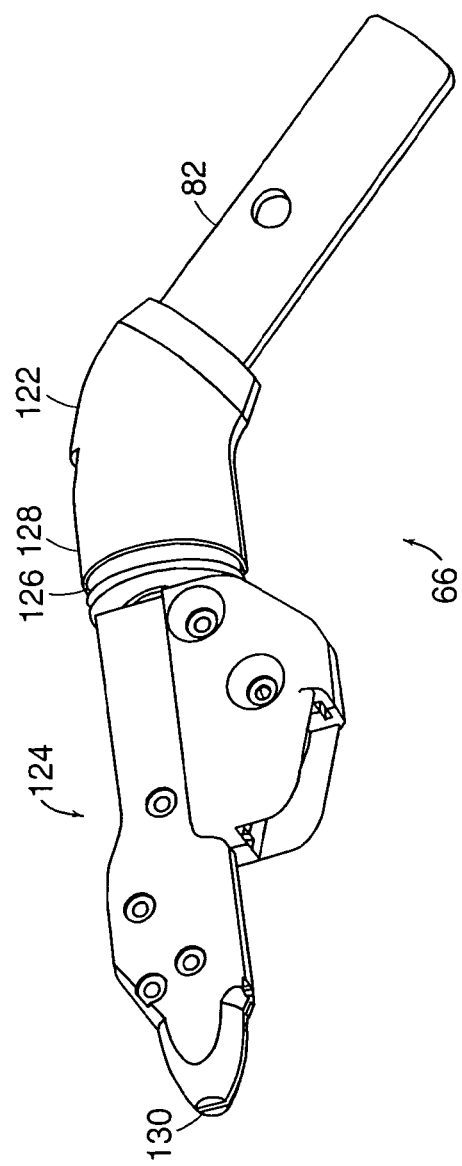

In yet another embodiment, the instrument can be adapted to facilitate access into the abdominal cavity and the placement of suture(s) radially in a body lumen. Such instrument may be particularly useful where anastomosis is required such as urethral anastomosis following radical prostatectomy or in blood vessel or bowel anastomosis. Referring to FIGS. 6A-6C, the suturing instrument 66 includes an elongated body member 82 and a rotatable head 124. The elongated body member 82 can include an elbow 122 (or bend). The head 124 rotates by angular increments. The elongated body member 82 includes an engaging element located at its distal end 128. The head 124 includes an engaging element located at its proximal end 126 for mating with the engaging element of the elongated body member 82. The head 124 includes a dilator cap or a bullet-shaped end at the distal end 130 of the head 124 to maintain the urethra or any body lumen in a dilated configuration. The rotation of the head 124 is performed manually between each application of a suture in a body lumen and before reloading with the needle and suture to permit application of a series of sutures along the circumference of the lumen, at incremental angular positions that can be as small as 10°. The embodiment of the suturing instrument featuring an elbow and rotatable head is particularly adapted to perform suturing after removal of the prostate to connect the bladder to the urethra or generally following any other type of resection.

Figure 6D:
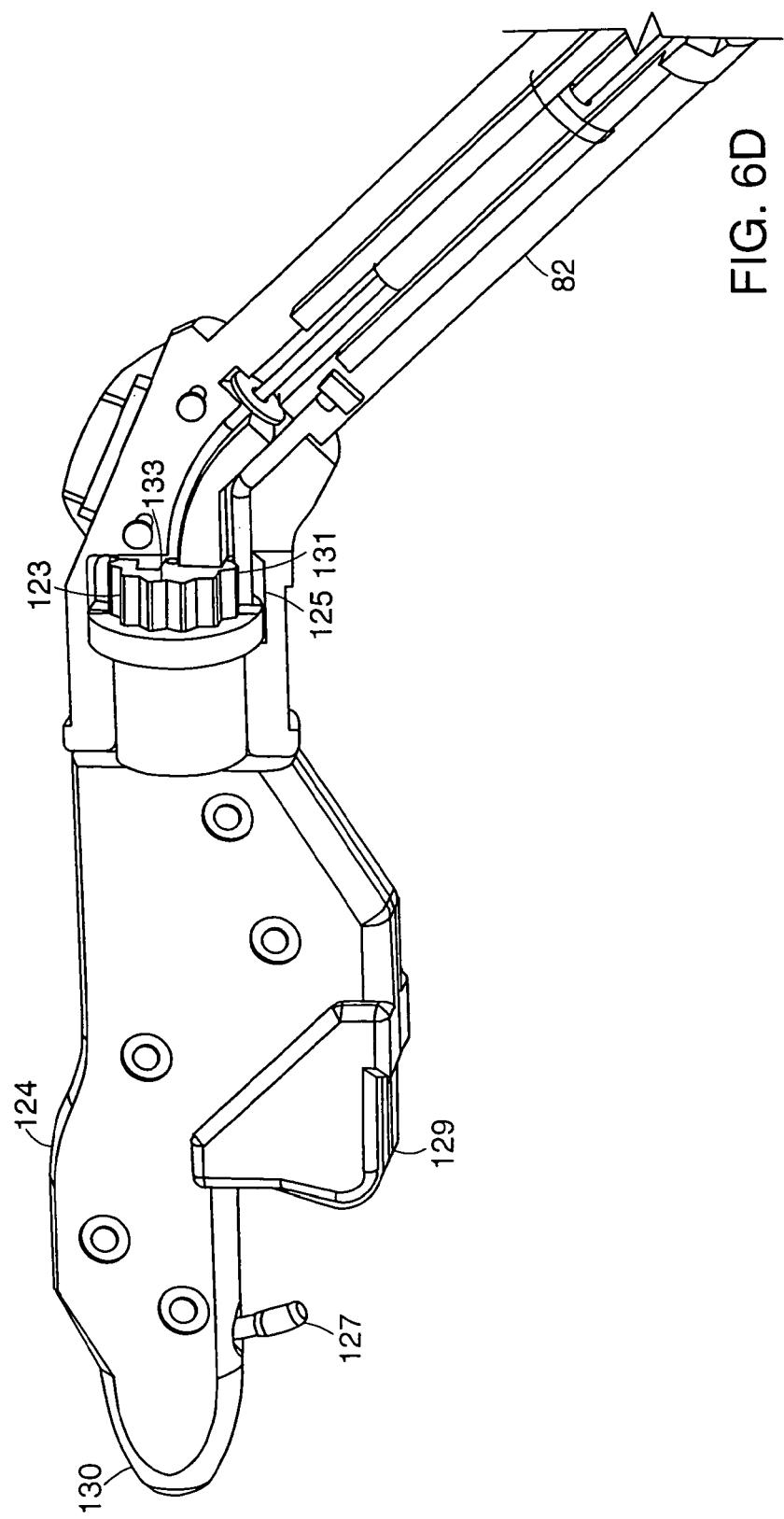

In one embodiment, the rotatability of the head 124 is accomplished with the structure depicted in FIGS. 6D-6F. The head 124 includes an engaging element with a male configuration 123. The male configuration 123 includes a series of fluted cuts 133 located along 330° of its perimeter. The male configuration 123 includes a stop to prevent the head from rotating 360°. The elongated body member 82 includes an engaging element with a female configuration 125 and a flexible detent 131. The female configuration 125 is a substantially circular recess with the flexible detent mounted within the elongated body member 82 and protruding into the substantially circular recess. The flexible detent 131 can be a length of spring wire or a pin, and can be made of nitinol. The head 124 can be positioned by rotating the male configuration 123 engaging element with respect to the female configuration 125 engaging element, deflecting the flexible detent 131, and then allowing the flexible detent 131 to mechanically engage the fluted cut 133 which corresponds to the desired angular orientation. The head can be positioned in angular increments of 30°. In addition, the head 124 depicted in FIGS. 6D-6F includes a needle deployment mechanism 127 and a needle catch mechanism 129.

Figure 7C:
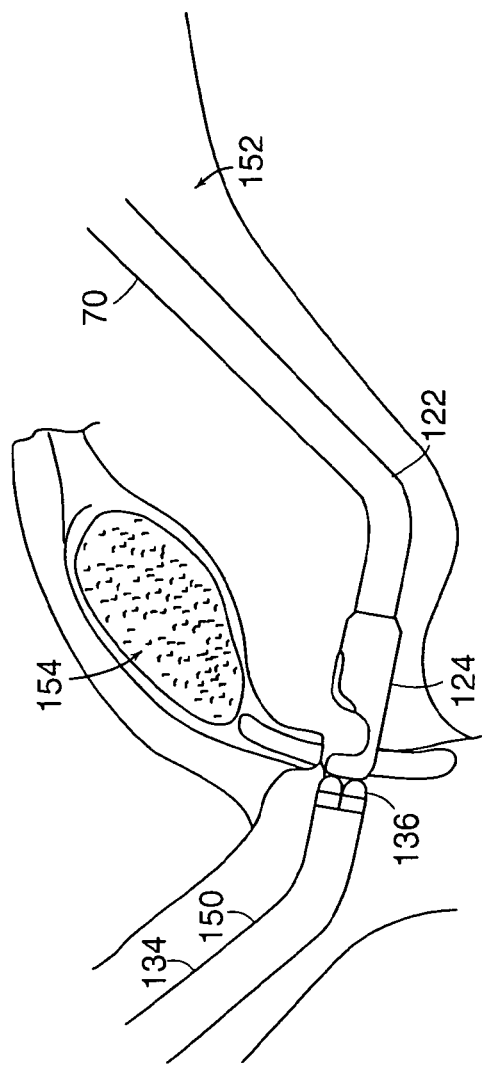
FIG. 7C is a schematic representation of one embodiment of a suturing system of the present invention shown located in the urethra and bladder.

Referring to FIGS. 7A-7C, to further facilitate positioning of the instrument within the body passageway, a grasper device 132 may be introduced into the body cavity by a second point of entry. The grasper device comprises a hollow elongated body member 134 for housing a pair of spring-loaded jaws or tweezers 136 at the distal end of the body member 134. The tweezers 136 are close together in a retracted position as shown in FIG. 7A and open to permit grasping of the knob 138 located on the distal end of the head 124 in an extended position as shown in FIG. 7B. When closed around the ball or knob 138, the grasping tweezers 136 can allow rotatable movement of the knob 138 and thus rotation of the head 124.

The proximal end of the grasper device 132 features a button 140 that is positioned at the proximal end of a wire 142. The wire 142 is connected to the tweezers 136 at the distal end. The device is maintained in the retracted position by a spring 144 located in the head 146 of the grasper 132 which rests its proximal end against the button 140 and its distal end against a protuberance 148 positioned in the interior wall of the head 146.

FIG. 7C shows both the grasper 132 and the suturing instrument 66 located in the urethra 150 and the bladder 152 below the public bone 154 of a male following prostatectomy. The void left by the removed prostate is addressed by using the instrument 66 together with the grasper 132 to insert sutures all around the end of the urethra 150 to join it to the bladder 152.

In yet other embodiments of the instant invention, the aforementioned suturing systems can be used to deploy an anchor or fastener that is to remain in the tissue. Such anchor or fastener may be; for example, a barbed needle, a metal clip, or a staple.

Having described embodiments of the invention, it will be apparent to one skilled in the art that other embodiments incorporating the concepts disclosed herein may be used without departing from the spirit of the invention. Thus, numerous other embodiments include, but are not limited to: changes in the dimensions of the instruments; the type of materials employed; the location and type of needle, anchor or fastener; and needle loading mechanisms. All are within the scope of the present invention. The described embodiments are to be considered in all respects only as illustrative and not restrictive. Therefore, it is intended that the scope of the present invention be only limited by the following claims.

The invention claimed is:

1. A suturing instrument, comprising:
an elongate body member having a lumen defined in a distal portion, the lumen extending through the elongate body member and defining an opening in the distal portion, the lumen having an inner wall that tapers inward at a distal end of the lumen; and
a needle deployment mechanism including:
a needle carrier including a needle holder disposed at a distal end of the needle carrier, a distal end of the needle holder having a hole defined therein;
a needle including a tapered body defining a shoulder and a neck disposed distally to the tapered body, the neck being removably disposed in the hole in the distal end of the needle holder; and
a catch having a slot defined therein, the catch being laterally separated from the needle carrier and the needle within the lumen,
the needle deployment mechanism being configured for distally deploying the catch, the needle carrier and the needle between respective retracted positions, in which the catch, the needle carrier and the needle are substantially disposed within the lumen, and respective extended positions, in which the catch, the needle and at least a portion of the needle carrier, including the needle holder, are extended distally out of the lumen and through the opening, the inner wall causing the catch, and the needle holder and the needle to be directed from the inner wall toward an intersecting point outside of the lumen when the catch, the needle carrier and the needle are deployed from their respective retracted positions to their respective extended positions.

2. The suturing instrument of claim 1, wherein the catch is configured to capture the needle and pull a suture coupled with the neck of the needle through a tissue as the needle carrier and the catch are returned from their respective extended positions to their respective retracted positions.

3. The suturing instrument of claim 1, wherein the opening is open in a distal direction.

4. The suturing instrument of claim 1, wherein the distal portion does not move relative to the elongate body member.

5. The suturing instrument of claim 1, further comprising a handle coupled with the elongate body member.

6. The suturing instrument of claim 5, wherein the elongate body member distally extends from the handle.

7. The suturing instrument of claim 1, further comprising an actuator coupled with the needle carrier and the catch, the actuator being configured to the deploy the catch, and the needle carrier and the needle from their respective retracted positions to their respective extended positions.

8. The suturing instrument of claim 7, wherein the actuator is at least partially disposed within a handle coupled with the elongate body member.

9. The suturing instrument of claim 1, wherein the catch and the needle carrier are configured, when in their respective extended positions, to operably couple the shoulder of the tapered body of the needle with the catch, the catch being configured to pull the needle from the needle carrier and pull the suture through a tissue as the needle carrier moves from the extended position to the retracted position.

10. A suturing instrument, comprising:
an elongate body member having a lumen defined in a distal portion, the lumen extending through the elongate body member and defining an opening in the distal portion, the lumen having an inner wall that tapers inward at a distal end of the lumen;
a needle carrier disposed within the lumen;
a needle removably disposed at a distal end of the needle carrier;
a catch laterally disposed opposite the needle carrier within the lumen, the catch including a convex member having a closed slot defined therethrough, the closed slot being configured to remove the needle from the needle carrier when in an extended position; and
an actuator configured to deploy the needle carrier and the catch from a retracted position from within the lumen to the extended position, which is at least partially outside the lumen, the inner wall causing the needle carrier and the catch to be directed toward each other such that the needle carrier and the catch intersect and the needle is directed through the closed slot in the catch when the needle carrier and the catch are deployed from the retraced position to the extended position.

11. The suturing instrument of claim 10, further comprising a suture coupled with the needle, the catch being configured to pull the needle and the suture through a tissue as the catch is moved from the extended position to the retracted position.

12. The suturing instrument of claim 10, further comprising a handle coupled with the elongate body member, the actuator being at least partially disposed within the handle.

13. A suturing instrument, comprising:
an elongate body member having a lumen defined in a distal portion, the lumen extending through the elongate body member and defining an opening in the distal portion, the lumen having an inner wall that tapers inward at a distal end of the lumen;
a needle carrier having a needle removably coupled therewith;
a needle catch including a convex member having a closed slot defined therethrough, the closed slot being configured to capture the needle as a result of the needle carrier and the needle catch intersecting when in an extended position; and a deployment mechanism including an actuator coupled with the needle carrier and the needle catch, the deployment mechanism being configured to distally deploy the needle carrier and the needle catch between a retracted position, in which the needle carrier and the needle catch are substantially disposed within the lumen, and the extended position, in which at least a portion of the needle carrier, including the needle, and at least a portion of the needle catch are extended distally out of the lumen and through the opening, the inner wall causing the needle carrier and the needle catch to be directed from the inner wall toward a center of the lumen and to intersect as needle carrier and the needle catch are deployed from the retracted position to the extended position.

14. The suturing instrument of claim 13, wherein the needle catch is configured to pull a suture coupled with the needle through a tissue as the needle catch moves from the extended position to the retracted position.

15. The suturing instrument of claim 13, wherein the opening is open in a distal direction.

16. The suturing instrument of claim 13, wherein the distal portion does not move relative to the elongate body member.

17. The suturing instrument of claim 13, wherein the needle catch includes at least one tissue piercing edge.

* * * * *